June 13, 1950 E. S. BOERNER Plant Pat. 948
ROSE PLANT
Filed April 6, 1949
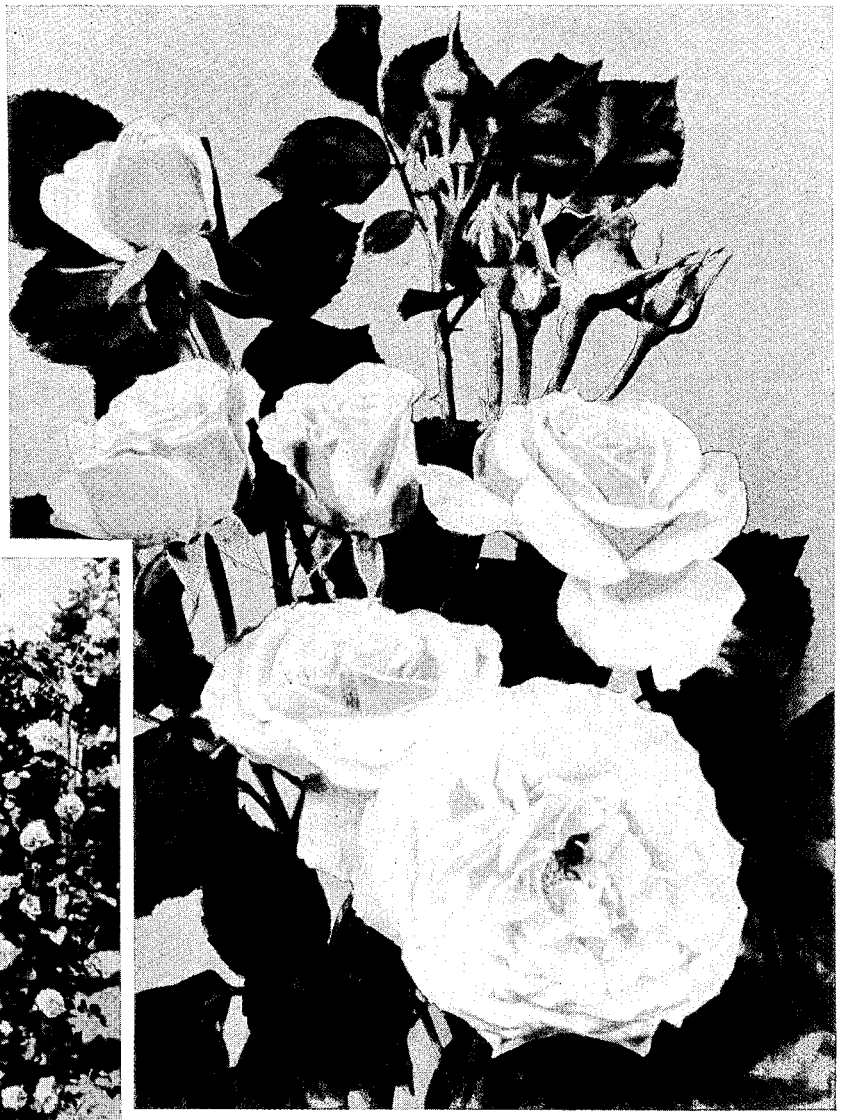
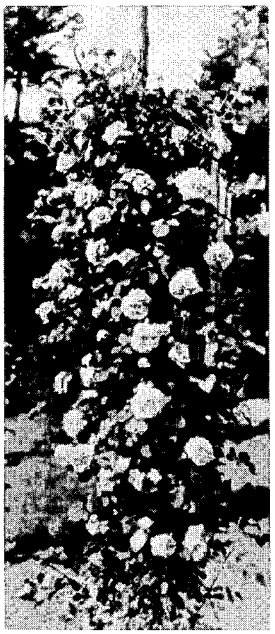
Inventor
E. S. Boerner
By Robb & Robb
by H. C. Robb
Attorneys Patented June 13, 1950

Plant Pat. 948

UNITED STATES PATENT OFFICE

948

ROSE PLANT

Eugene S. Boerner, Newark, N. Y., assignor to Jackson & Perkins Company, Newark, N. Y., a corporation of New York Application April 6, 1949, Serial No. 85,778

1 Claim. (Cl. 47—61)

The present invention relates to a new and distinct variety of rose plant, originated by crossing the well-known varieties "Mercedes Gallart," a very fragrant, deep pink climbing hybrid tea, and "New Dawn," also a climber of shell pink color, thereby combining in the new rose important dominating characteristics of both parents, including the color of the flowers which is distinctly different and new in the rose world.

The color of this new rose is distinguished from that of the seed parent which is Tyrian Rose (Plate 12, Ridgway) and sometimes during the blooming season Rhodamine Purple (Plate 12), in that these colorings are reduced in intensity by the shell pink of "New Dawn" to a very pleasant pink shade, as hereinafter more specifically described.

The shape of the flower of this new variety is similar to that of "Mercedes Gallart," but the size is a little smaller.

This new variety is, moreover, characterized as to novelty by the production of double, fragrant blooms on a pillar type of plant, as shown in the black and white figure of the accompanying drawings; by its remontance throughout the summer season, and by its heavy, shiny, disease resistant foliage, similar to its parent "Mercedes Gallart," but smaller in size.

In the accompanying original drawing, the illustration in color shows specimens of this new variety at different stages of development of the foliage and of the flowers from bud to full-opened blooms, particularly depicting as nearly as possible their soft pleasing pink coloring; and in the black and white figure of the drawing is clearly shown the pillar type of growth of this new variety.

The following is a detailed description of the new variety, color terminology being in accordance with Ridgway's Color Standards and Nomenclature:

Parentage: Seedling.

*Seed parent.*—"Mercedes Gallart" (unpatented).

*Pollen parent.*—"New Dawn" (Pl. Pat. No. 1).

Classification: Botanic and commercial—climber.

Place where asexually reproduced: Newark, New York.

Method of reproduction: Budding.

*Flower*

(The following observations made outdoors at Newark, New York, in the afternoon in the month of September.)

Blooming habit: Recurrent—continuous.

Bud:

*Size.*—Large.

*Form.*—Globular. Is not affected by wet or hot weather.

*Color.*—When sepals first divide—Oxblood Red, plate 1. When petals begin to unfurl—Pomegranate Purple, Plate 12. When half blown—inside of petals—Deep Rose Pink, Plate 12; Reverse of petals—Lower half—Rose Red, Plate 12, upper half—Amaranth Pink, Plate 12.

*Sepals.*—Branched, "hood" above bud. Curl back when petals begin to unfurl. Color—inside—Glass Green, Plate 31; outside—Biscay Green, Plate 17.

*Calyx.* — Shape—pear. Size — small. Aspect—smooth. Odor when rubbed—none. Color—Absinthe Green, Plate 31.

*Peduncle.* — Length — medium. Aspect—smooth. Color—Buffy Citrine, Plate 16. Strength—Erect; heavy.

*Opening.*—Bud opens up well. Is not affected by adverse weather conditions.

Bloom:

*Size.*—Large. Average size when fully expanded, 3½".

*Borne.*—Singly and several together.

*Stems.*—Long; strong.

*Form.*—When first open—cupped. Permanence—flattens and outer petals curl back.

*Petalage.*—Very double (many petals and stamens hidden). Number of petals under normal conditions—55-60.

*Color.*—Center of flower—Deep Rose Pink, Plate 12. Outer petals—Rose Pink, Plate 12. Base of petals (aiglet)—Citron Yellow, Plate 16. Inside of petals—Rose Pink, Plate 12. Reverse of petals—Deep Rose Pink, Plate 12; lower half of petal Rose Red, Plate 12. General tonality from a distance—Rose Pink, Plate 12.

*Discoloration.*—General tonality at end of first day—Deep Rose Pink, Plate 12. Second day—Rose Pink, Plate 12. Third day—Cameo Pink, Plate 26.

Petals:

*Texture.*—Thick. Is not affected by wet or hot weather.

*Appearance.*—Inside and outside shiny.

*Form.*—Oval.

*Arrangement.*—Irregular. Petaloids in center—many; small.

*Persistance.*—Drop off cleanly.

*Fragrance.*—Moderate. Nature—tea (average hybrid tea scent).

*Lasting quality.*—On the plant and as cut flower—long.

Genital organs:

*Stamens, anthers.*—Large; many. Color—Light Cadmium, Plate 4. Arrangement—regular around styles.

*Stamens, filaments (threads).* — Medium length. Color—Buff Yellow, Plate 4.

*Pollen.*—Color—Maize Yellow, Plate 4.

*Styles.*—Columnar, uneven length; medium long; thin.

*Stigmas.*—Color—Baryta Yellow, Plate 4.

*Ovaries.*—All enclosed in calyx.

*Plant*

Form: Climber.

Growth: Very vigorous; branching.

Foliage: 5 to 7 leaflets.

*Size.*—Large.

*Quantity.*—Abundant.

*Color.*—New foliage: upper side—Yellowish Oil Green, Plate 5, outer edges Victoria Lake, Plate 1; under side—Victoria Lake, Plate 1; mid-rib Yellowish Oil Green, Plate 5. Old foliage: upper side—Dark Cress Green, Plate 31; under side—Light Elm Green, Plate 17.

*Shape.*—Oval pointed.

*Texture.*—Upper side — leathery; under side—smooth. Ribs and veins—prominent.

*Edge.*—Serrated (saw toothed).

*Serration.*—Single; sharp.

*Leaf stem.*—Color—Biscay Green, Plate 17. Under side—prickles.

*Stipules.*—Long; smooth.

*Disease resistance.*—Resistant.

Wood:

*New wood.*—Color—Mineral Red, Plate 27. Bark—smooth.

*Old wood.*—Color—Bice Green, Plate 17. Bark—smooth.

Thorns:

*Thorns.*—Quantity—on main stalks from base and on laterals from stalk—many. Form—broad base; long; hooked downward. Color when young—Garnet Brown, Plate 1. Position—irregular.

*Prickles and hairs.*—None.

I claim:

A new and distinct variety of rose plant characterized as to novelty by its pillar habit of growth; the pleasing and soft pink coloring of the blossoms; the remontance habit of blooming throughout the summer season; the fragrance of its double blooms; and its heavy, shiny, disease resistant foliage, substantially as shown and described.

EUGENE S. BOERNER.

No references cited.